United States Patent
Montanari et al.

(10) Patent No.: US 7,846,483 B2
(45) Date of Patent: Dec. 7, 2010

(54) COSMETIC COMPOSITION FOR SKIN APPLICATION SUITABLE FOR RELAXING EXPRESSION WRINKLES

(75) Inventors: Daniela Montanari, Albignasego-Padova (IT); Manuela Guglielmo, Vigonovo-Venezia (IT)

(73) Assignee: Labo Cosprophar AG, Basel (CH)

( * ) Notice: Subject to any disclaimer, the term of this patent is extended or adjusted under 35 U.S.C. 154(b) by 716 days.

(21) Appl. No.: 10/583,816

(22) PCT Filed: Mar. 8, 2005

(86) PCT No.: PCT/EP2005/002477

§ 371 (c)(1),
(2), (4) Date: Jan. 12, 2007

(87) PCT Pub. No.: WO2006/069608

PCT Pub. Date: Jul. 6, 2006

(65) Prior Publication Data

US 2007/0148118 A1    Jun. 28, 2007

(30) Foreign Application Priority Data

Dec. 29, 2004   (CH) .................................. 2164/04
Feb. 1, 2005    (CH) .................................. 0144/05

(51) Int. Cl.
*A61K 8/19*   (2006.01)
*A61K 8/64*   (2006.01)
*A61K 38/05*  (2006.01)
*A61K 38/08*  (2006.01)

(52) U.S. Cl. ................. 424/777; 424/722; 514/17; 514/20; 514/557; 514/844

(58) Field of Classification Search ............... None
See application file for complete search history.

(56) References Cited

U.S. PATENT DOCUMENTS

| | | | | |
|---|---|---|---|---|
| 5,563,041 | A * | 10/1996 | Reers ........................ | 435/13 |
| 5,607,858 | A * | 3/1997 | Stuber et al. .............. | 436/69 |
| 6,277,404 | B1 * | 8/2001 | Laversanne et al. ........ | 424/450 |
| 6,338,855 | B1 * | 1/2002 | Albacarys et al. .......... | 424/409 |
| 2004/0120918 | A1 * | 6/2004 | Lintner et al. ............ | 424/70.14 |
| 2004/0132667 | A1 * | 7/2004 | Lintner ..................... | 514/18 |
| 2004/0147443 | A1 * | 7/2004 | Renault ..................... | 514/12 |
| 2005/0002996 | A1 * | 1/2005 | Sojka ........................ | 424/445 |
| 2005/0074461 | A1 * | 4/2005 | Donovan .................. | 424/184.1 |
| 2006/0052287 | A1 * | 3/2006 | Patt ........................... | 514/6 |

FOREIGN PATENT DOCUMENTS

| | | | |
|---|---|---|---|
| FR | 2786693 A1 | * | 6/2000 |
| JP | 2004-197234 A | * | 3/2004 |

* cited by examiner

*Primary Examiner*—Jeffrey E Russel
(74) *Attorney, Agent, or Firm*—Hedman & Costigan, P.C.; James V. Costigan

(57) ABSTRACT

The present invention relates to a cosmetic composition for skin application suitable for relaxing expression wrinkles which combines a selected active peptide component with a decontracting or relaxing action on the muscular fiber with a micro-element which reduces the muscular contraction level by acting directly or indirectly on a muscular fiber component. The active principles of the cosmetic composition of the invention are conveniently carried by liposomes.

4 Claims, 4 Drawing Sheets

DEPENDENCE OF THE OUTGOING FLOW OF CALCIUM IONS ON THE EXTERNAL CONCENTRATION OF MAGNESIUM IONS

COSMETIC COMPOSITION FOR SKIN APPLICATION SUITABLE FOR RELAXING EXPRESSION WRINKLES

The present invention relates to a cosmetic composition for skin application suitable for relaxing expression wrinkles.

Face wrinkles are more or less linear furrows present on the skin of the face, of varying depths, considered as being a sign of skin aging.

The causes of the formation of wrinkles can be mainly attributed to the combined action of the following factors:

i) overall chronological skin aging, ii) force of gravity, iii) degradation of the elastic and collagen fibers due to the action of sunlight; iv) consequence of repeated muscular and articular movements.

These factors influence in different ways the formation of wrinkles depending on whether these are age wrinkles, gravitational wrinkles, actinic wrinkles or expression wrinkles.

Age wrinkles are formed as a result of a reduction in the thickness of the derma and a decrease in the number of fibroblasts present, as well as a slow-down in the cellular turnover and cellular metabolism itself.

Gravitational wrinkles appear when the elastic fibers and altered collagen bundles of the derma are no longer capable of counterbalancing the force of gravity and appear physiologically in the aging process of the organism.

Actinic wrinkles are due to the cumulative damage exerted by sun radiation on the elastic and collagen fibers. They are present in the photo-exposed regions. They correspond to a more or less marked accentuation of the skin weave which creates a series of fine widely-spread wrinkles.

Expression or mimic muscle wrinkles are furrows which are formed on the skin of the face essentially as a result of the repetitive traction exerted by mimic muscles.

At the age of thirty, expression wrinkles are already clearly visible but with the advancing of age, they become progressively deeper. They are considered as being dynamic wrinkles and consequently in direct relation with contractive muscular energy and the number of contractions. These wrinkles are more evident in individuals who widely use facial mimicking, they are more marked in various high dynamism points of the face such as around the mouth or eyes, on the forehead by wrinkling or on the side most frequently used for expression.

In order to have a better understanding of their nature and origin, it should be noted that facial mimic muscles are related to the contours of the eye-sockets, eyelids, nose, lips, cheeks, mouth, auricles, scalp and skin of the neck. Facial mimic muscles are small and fine, they have the common factor of having a cutaneous nerve ending and can be elevator, depressor, constrictor or dilator muscles. They have a double role: functional and exteriorization of the individual's mental functions. Almost all of them are to be found in the subcutaneous connective of the front part of the face. From their deep insertion in the bone stratum of the face, they rise to the surface towards the skin where, at the level of the deep dermal stratum, they have their surface insertion. Their contraction causes the movement of the facial skin, with the formation of folds which are always perpendicular to the direction of the muscular fibers. These folds cause a modification of the facial features which is specific for that particular muscle and can be considered as being a dynamic expression of the personality, character or particular state of mind.

Facial muscles, as all muscular tissues, are made up of muscular fibers (each muscular fiber is a single muscular cell) consisting of hundreds of long contractile bundles called myofibrils in turn consisting of contractile strands. The nerve fibers innervate the muscular fiber through branchings terminating in swellings called synaptic buttons. When the nerve stimulus, which induces contraction, reaches the end of the nerve fiber, at the level of the synaptic button there is the accumulation of a large number of vesicles containing the neurohumor acetylcholine which, following the fusion of the vesicles themselves with the neuron membrane, is released in large quantities within the space passing between the synaptic button and the muscular fiber (synaptic space).

Once the acetylcholine molecules have been released, they bind themselves to specific receptors, or canal proteins which pass, for the whole thickness, through the plasmatic membrane of the muscular cell. These canal receptors are generally closed and remain so until various acetylcholine molecules become bound with them causing their opening. With the opening of these receptor canals of acetylcholine there is an overall passage of large quantities of positive ions ($Na^+$ sodium ions) inside the muscular cell. This flow of $Na^+$ ions causes an inversion in the polarity of the muscular plasmatic membrane: the so-called depolarization of the membrane which leads to the creation of an action potential. Once created, the action potential propagates from where the stimulus has been applied to the successive membrane area, causing its depolarization.

The action potential induces the release, in the cytoplasm of the cell, of $Ca^{2+}$ calcium ions on the part of the endoplasmic reticulum, an organelle present inside the muscular cell which contains large concentrations of calcium ions. Their release takes place as a result of the opening of the voltage-dependent canals present in the reticulum membrane which, under the effect of the action potential, open, discharging the calcium ions. At this point, when calcium is released into the cytoplasm of the muscular cell, all the contractile strands present therein are rapidly activated causing the contraction of the muscle. The calcium therefore acts as an actual switch capable of triggering muscular contraction.

Recent anti-wrinkle treatment is specifically based on interaction with the nerve impulse transmission systems to muscular fibers on the part of a potentially toxic substance, botulinus toxin.

Botulinus toxin, commonly referred to as Botulin, is produced by a bacterium, *Clostridium Botulinum*, the cause of infections which can also cause a person's death by paralysis of the respiratory muscles following stoppage of the release of acetylcholine at the level of the nerve endings on the musculature with the consequent blockage of the nerve impulse transmission to the muscular membrane.

The discovery of its action mechanism has transformed this toxin into a drug capable of attenuating, over approximately 20 years, many pathological situations such as: hereditary strabismus, blepharospasm, spasms at the joints, serious incontinence.

As of 1992, a Canadian dermatologist had the idea of using botulinus toxin in the cosmetic field for relaxing glabellar wrinkles, i.e. the vertical lines situated above the eyebrows. This idea became increasingly applied in non-therapeutic fields but its application for purely aesthetic purposes was only approved of by the FDA in 2002. Injected in small doses by means of cutaneous micro-injections into expression wrinkles by plastic surgeons and dermatologists, it relaxes wrinkles as it decontracts the muscles. In Italy, approval was obtained in April 2004, for exclusive use on the part of plastic surgeons, maxillo-facial specialists, dermatologists and ophthalmologists.

The use of Botulinus Toxin for aesthetic purposes, by means of cutaneous micro-injections, is mainly envisaged for relaxing vertical expression wrinkles of the forehead, between the eyebrows. Its use has generally been extended however to the upper third of the face (forehead, glabella, eyes).

Although treatment with botulinus toxin has revolutionized the cosmetic approach of the treatment of face wrinkles, its use is not without disadvantages which can also be serious.

Possible risks connected with injections of Botulinus toxin for aesthetic purposes, such as pain in the treated area, erythema, nausea, swelling, are widely known and documented in scientific literature. An excessive quantity can also cause expression fixture whereas an error in the inoculum can cause a lowering of the eyebrow or eyelids.

In view of what is specified above, the necessity for availing of cosmetic products for relaxing expression wrinkles by means of a topic and consequently non-invasive application, thus reducing the inherent risks in these aesthetic treatment methods, is evident.

An objective of the present invention consists in supplying a composition and cosmetic method capable of causing an effective relaxation of expression wrinkles without resorting to a harsh administration method (micro-injection) of the active principles.

Another objective of the invention consists in providing a cosmetic composition capable of relaxing expression wrinkles without causing the formation of side-effects typical of the local application of botulin.

A further objective of the invention consists in providing a cosmetic composition free of botulinus toxin which is capable of reducing cutaneous micro-contractions of the face producing a relaxation effect of expression wrinkles causing their attenuation or disappearance.

The objectives of the present invention are achieved by providing a composition for cosmetic use suitable for relaxing expression wrinkles comprising at least ore peptide with a decontracting action on the muscular fiber, at least one micro-element which reduces the contraction of a muscular fiber and a cosmetically acceptable carrier. Further characteristics of the invention are specified in the subsequent claims.

The present invention derives from the affirmation that by combining a selected peptide component having a decontracting or relaxing action on the muscular fiber with a micro-element which reduces the muscular contraction level by acting directly or indirectly on a component of the muscular fiber, a synergic wrinkle-relaxing action is obtained. This relaxing action is particularly evident with respect to expression wrinkles.

According to a first aspect of the invention, a cosmetic composition is therefore provided, based on active principles which, by acting by means of direct and/or indirect mechanisms on various action sites at the level of the cell or muscular fiber, produce a synergic relaxing action on the fiber itself which causes a particularly appreciable relaxation of the expression wrinkle from an aesthetic point of view.

In accordance with a first aspect of the invention, the Applicant has found that the synergic relaxing action on wrinkles is particularly marked when the active peptide component of the composition comprises a pentapeptide containing the following amino acids: alanine (ala), arginine (arg), proline (pro), glycine (gly).

Figure 1:
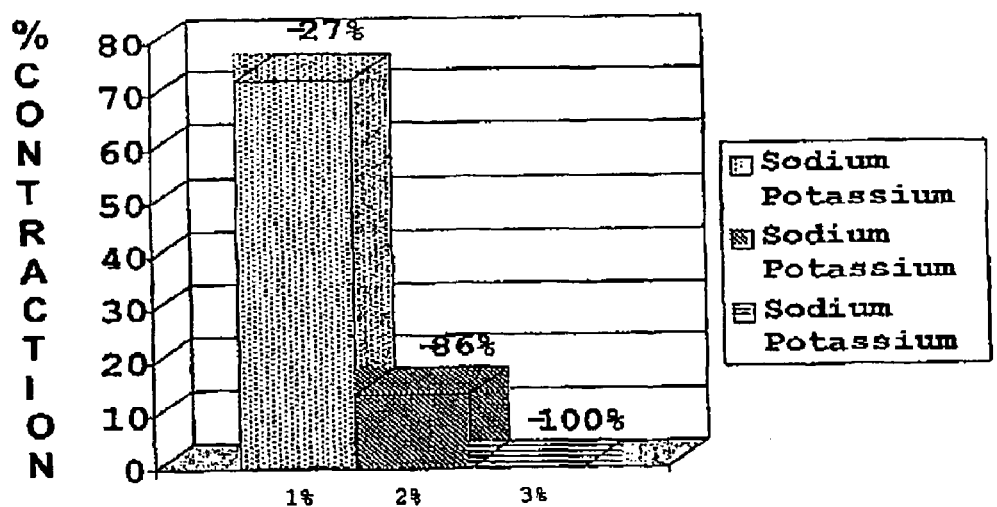
FIG. 1 is a graph which shows the percentage decrease in muscular fiber concentration versus the concentration of sodium and potassium.

According to a preferred embodiment, said peptide component consists of 5 amino acids with a curare-like activity and preferably comprises the following sequence: GLY-PRO-ARG-PRO-ALA SEQ ID NO 1.

On a synaptic level, the GLY-PRO-ARG-PRO-ALA SEQ ID NO 1. competes with the acetylcholine neurotransmitter in the bond with its receptor, which is present at the level of the membrane of the muscular cell and has a canal-shaped structure. These canal receptors are generally closed and remain so until various acetylcholine molecules bind with them causing their opening. Following the bond of said pentapeptide in the place of acetylcholine, the canals remain closed and consequently there is no passage of positive ions ($Na^+$ sodium ions) inside the muscular cell, necessary for causing the depolarization of the membrane and consequently the muscular contraction does not occur due to the non-accumulation of calcium ions.

Typically, a pentapeptide of the gly-pro-arg-pro-ala-$NH_2$ SEQ ID NO 1. type, which is particularly suitable for the application of the invention, can be obtained by means of a chemical synthesis process in solid phase. According to this synthesis procedure, the pentapeptide is synthesized using a polymeric solid carrier, such as, for example, the chlorotritylchloride-2 resin to which the amino acids are bound in succession, starting from the first one. The latter can be used in a suitably modified form so that it is bound to the resin and remains protected (Fmoc-protection) by the action of the reagents used during the polypeptide synthesis.

One or more series of purification phases conveniently follow, typically by means of ion exchange chromatography and gel chromatography which lead to the production of the purified oligopeptide.

According to an embodiment, the active peptide component of the composition of the invention comprises a gly-pro-arg-pro-ala-$NH_2$ pentapeptide SEQ ID NO 1, associated with a dipeptide having a decontracting or relaxing action of the muscular fiber, conveniently comprising the amino acids tyrosine and arginine which intervene in the neurotransmission processes causing a relaxation of the muscular, fiber and the consequent relaxation of the musculature itself.

In particular, said tyrosine arginine dipeptide:
  in the neurons of the central nervous system (CNS) stimulates the gene expression of the POMC (Pro-opiomelanocortine) gene precursor of metenkefaline, the neuropeptide involved in the relaxation of the musculature
  reduces the CGRP (Calcitonin Gene Related Peptide) synthesis, the neuropeptide involved in stimulating the muscular activity. Whereas on the one hand, acetylcholine produces a contraction of the muscular fibres, on the other, the CGRP stimulates the production of cyclic AMP which, through a series of chain phosphorylations, reinforces the tone of the contraction and activates the production of energy in the muscular cell.

According to an embodiment, the tyrosine-arginine dipeptide is acetylated to make it more lipophilic, more stable and bio-available on a cutaneous level. Acetyl tyrosine-arginine -1 cetyl ester, a form capable of effectively modulating the release of neurohumors, is particularly suitable for skin and cosmetic application.

According to another embodiment, the cosmetic composition comprises an association with one or both penta/di-peptide components previously described with a micro-element which reduces the level of muscular contraction.

Within the scope of the invention, the term micro-element refers to physiologically acceptable inorganic elements which exert an action and an intervene in providing nerve stimuli to muscular fibers. Suitable micro-elements within the scope of the invention comprise one or more micro-elements selected from sodium, potassium, magnesium, their salts and physiologically acceptable derivatives.

The contemporaneous presence of the micro-elements sodium, potassium and magnesium, is particularly advantageous as, by acting with different mechanisms described further on, these micro-elements cause the closure of two access points of the muscular cell, considerably limiting the release of calcium ions therefrom and preventing the muscular contraction mechanism.

It has been observed in "in vitro" tests, that the administration at a level of the neuro-muscular synapses of a combination of sodium and potassium causes a myorelaxing action and which results in a consequent relaxation of expression wrinkles.

In this respect, the Applicant has also identified in the aqueous-based extract of anise, a natural source which is rich in sodium and above all potassium salts. Its action mechanism of the myorelaxing type is specifically linked to the potassium which blocks the sodium-potassium pump present at the level of the muscular cell membrane, forestalling the inlet of sodium and preventing the contraction of the muscular myofibrils. The non-introduction of sodium and strong presence of potassium outside the muscular cell prevents the depolarization of the membrane and the opening of the calcium canals situated at the level of the endoplasmic reticulum of the muscular cell. The non-accumulation of said calcium ions in the cell prevents the myofibrils contained inside the muscular cell from contracting, thus avoiding the contraction of the whole muscle.

Anise extract therefore represents a natural source of sodium-potassium which is particularly suitable for producing a cosmetic composition for fighting expression wrinkles.

A suitable aqueous solution rich in $Na^+$ salts and above all $K^+$ salts is obtained by aqueous extraction from *Pimpinella Asinum* fruit using water as solvent and a raw material/extract ratio equal to ½. The extraction process typically comprises the dissolution of the anise fruit in water, subsequent enzymatic hydrolysis, separation of the soluble and insoluble phases, filtration and optionally a final sterile filtration.

Typically, the presence, inside the cosmetic composition of the invention, of magnesium and/or its salts/derivatives can also be important for the purposes of the final anti-wrinkle effect as this micro-element exerts a decontracting activity on the musculature, as demonstrated by the "in vitro" tests effected.

Magnesium does in fact cause a reduction in the concentration of Calcium ions by interfering with the voltage-dependent Calcium canals present at the level of the endoplasmic reticulum of the muscular cell. By preventing these from opening, the magnesium prevents the release of the calcium ions crammed in the reticulum. By inhibiting their release, the stimulus to contraction is also inhibited.

Figure 2:
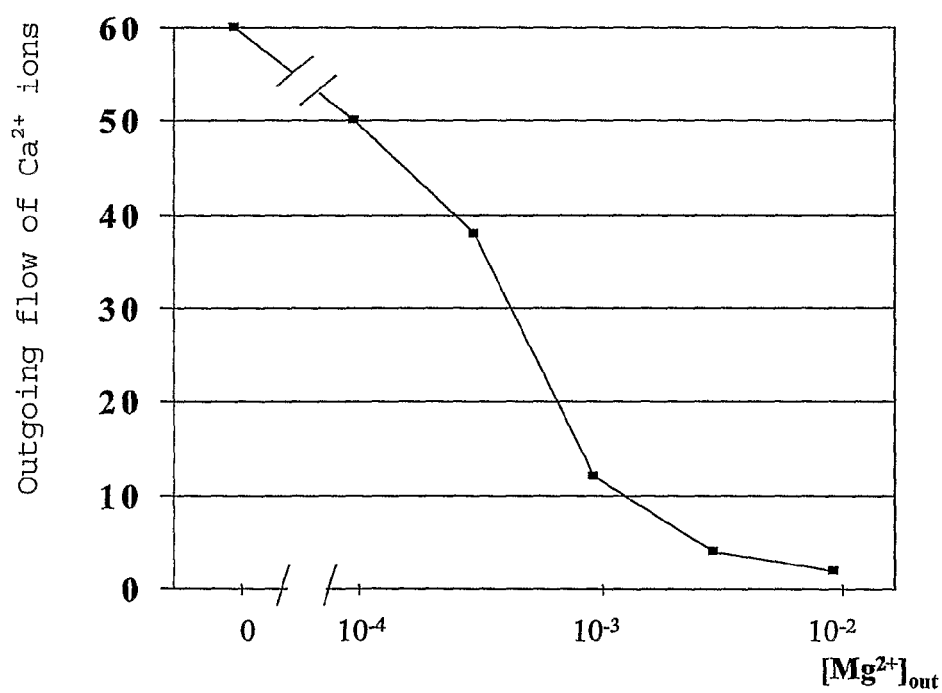
FIG. 2 is a graph which shows the dependence of the outflow of calcium ions versus the external concentration of magnesium ions.

It has been experimentally demonstrated that by varying the concentration of Magnesium ions in various periods, the quantity of Calcium ions that is released from the endoplasmic reticulum vesicles decreases with an increase in the same concentration of $Mg^{++}$ present in the medium. In particular, the dependence of the flow at the outlet of the calcium ions on the external concentration of magnesium ions was evaluated. The results obtained are shown in the graph of FIG. 2.

Among the different derivatives of magnesium which can be used within the scope of the invention, magnesium gluconate has proved to be particularly appreciable for use within a cosmetic composition.

According to a particular preferred embodiment, the cosmetic composition of the invention comprises a combination of a pentapeptide of gly-pro-arg-pro-ala SEQ ID NO 1. 1 with a dipeptide of acetyl tyrosine-arginine and sodium, potassium and magnesium gluconate micro-elements. The continuative topic application of this composition on the areas of the body requiring anti-wrinkle treatment against expression wrinkles induces a relaxation of the muscular fibers, as shown by the "in vitro" tests, causing, for example, a reduction in the depth of the wrinkles formed by repeated contractions of movements of facial expression muscles.

According to an embodiment, the composition of the invention comprises:

from 0.001% to 5% by weight of Sodium and Potassium from 0.001% to 5% of Magnesium gluconate from 0.001% to 5% of acetyl tyrosyl-arginyl(dipeptide)-1 -cetyl Ester from 0.001% to 5% of gly-pro-arg-pro-ala-$NH_2$ SEQ ID NO 1, The Applicant envisages the use of these active principles in increasing dosages in relation to the gravity of the wrinkles which can be defined according to an evaluation scale which however is not exhaustive, such as moderate wrinkles, deep wrinkles and very deep wrinkles.

In order to relax expression wrinkles, the above active principles operate synergically on the decontraction mechanism of the muscular cell, according to the following action procedures:

Pentapeptide of gly-pro-arg-pro-ala-$NH_2$ SEQ ID NO 1. mainly acts on the post-synaptic membrane. Said pentapeptide is a competitive antagonist of membrane receptors for acetylcholine (Ach). When the membrane receptors for acetylcholine are blocked, the ion canals remain closed. The sodium ions do not pass inside the muscular cell, the release of calcium ions is consequently not induced and the muscle remains relaxed, with the consequent relaxation of the surface tissues and softening of the wrinkles.

The association of sodium and potassium has the property of acting on the sodium-potassium pumps presents at the level of the muscular cell membrane blocking it and consequently preventing the opening of the calcium canals. The non-accumulation of calcium ions in the muscular cell ensures that the contraction does not take place.

Magnesium is an antagonist of calcium and inhibits its release on the part of the voltage-dependent calcium canals present on the endoplasmic reticulum of the muscular cell. By inhibiting their release the stimulus for contraction is also inhibited.

Acetyl dipeptide of tyrosine-arginine 1 cetyl ester stimulates the synthesis of the messenger neuropeptides of muscular relaxation and inhibits the synthesis of the messenger mediators of muscular contraction.

Figure 3:
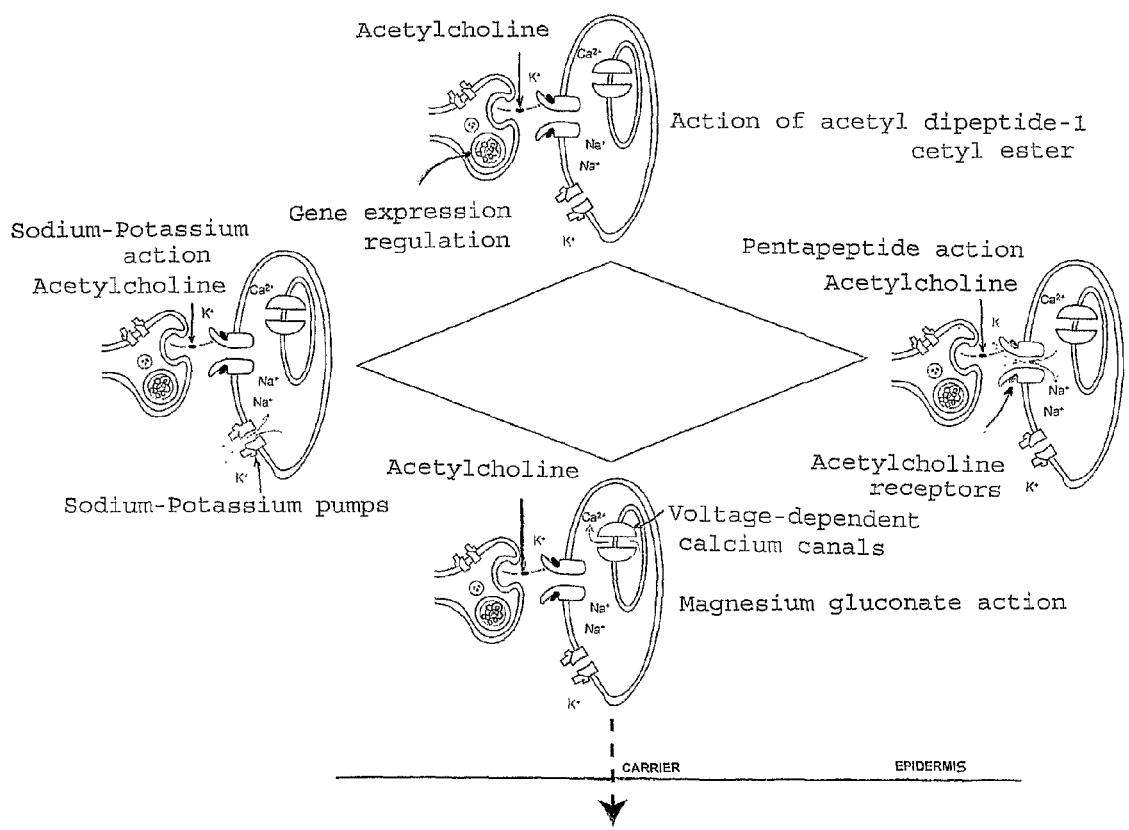
FIG. 3 is a schematic diagram which shows the interaction of sodium and potassium ions on acetyl choline and the actions of the pentapeptide on acetyl choline.

The decontracting synergic activity of facial muscles according to a preferred embodiment of the preparation, object of the invention, is expressed by a combination of these different action mechanisms, illustrated in enclosed FIG. 3.

The cosmetic compositions or preparations of the invention are provided in any suitable form for skin application, such as creams, emulsions, lotions, gels, oils, pastes, ointments, sprays, etc. for obstructing and reducing cutaneous micro-contractions with the final effect of relaxing expression wrinkles.

The equipment currently available for the technology according to customary procedures for experts in the field, is used for the preparation of the compositions.

One or more of the active principles are added and dispersed inside a physiologically acceptable carrier according to procedures known to experts in the field, conveniently adding one or more additives such as stabilizers, emulsifying agents, excipients, preservatives, aromas and suspending agents.

To extend their activity and provide a better performance through the skin, said active principles can be enclosed in a transporter or carrier comprising liposomes which gradually release them into the action site. The use of liposomes has the purpose of facilitating the penetration of the active principles as far as the action site. The liposomes used are preferably of the multilamellar type and conveniently have dimensions within the range of 150-500 nm. The particles generally have more than 5 lamellas and their concentric rings are slowly degrading; they gradually release their contents which are externally diffused as the concentration in the outer phase diminishes. The high number of lamellas allows a better retention of the hydrosoluble molecules with respect to other types of vesicles.

In particular, the liposomes used in the preparation/composition, object of the invention, are of the pro-liposome type, i.e. liposomes which are formed during the processing phases of the preparation. The phospholipids are conveniently provided in the form of disorderly assembled bilayers and the formation of the liposomes is triggered by the addition, under stirring, of a suitable quantity of water in excess with respect to the mixture of active principles.

The application of the cosmetic composition on the skin of the face can be effected directly with the fingers and/or using a method, already submitted as patent application, which allows the preparation to be spread directly on the furrow of the wrinkle by means of a graded syringe precision applier, equipped with a cannula for external application with a truncated end. Due to the precision application of the cosmetic preparation, this application device (Swiss patent application Nr. 01714/04) represents an innovation as it allows the preparation to be precisely applied directly to the furrow of the wrinkles, also improving the efficacy of the composition itself, object of the present patent.

It is also possible for the active principles to be freely dispersed in a cosmetic preparation and this use is preferably but not exclusively effected in continuation products aimed at being freely distributed on the facial skin, rather than on the furrow of the wrinkle.

The following examples are provided for purely illustrative purposes of the present invention and should in no way be considered as limiting its protection scope, as specified in the enclosed claims.

EXAMPLE 1

Formulation of a Cosmetic Composition According to the Invention, with Liposomes, Suitable as an Attack Preparation and Called Botoina® for Endermic Applications:
- 1% by weight of pentapeptide of gly-pro-arg-pro-ala-$NH_2$ SEQ ID NO 1.
- 4% by weight of anise extract
- 1% of Magnesium gluconate
- 2% of acetyl tyrosyl-arginyl (Dipeptide)-1 cetyl Ester
- 6-8% of liquid paraffin
- 5-7% of polyisoprene
- 0.1-1% of stearylic alcohol 25-ethoxylate
- 1-2% of coccus-polypeptide of wheat
- 1-2% of wheat proteins esterified with palmitic acid
- 1-3% of glyceryl isostearate
- 1-3% of propylene glycol
- 0-1% of lanolin oil
- 1% of dimethicone
- 0.1-1% of lecithin
- 0.001-0.1% of glycerin-0.001-0.1% of alcohol
- preservatives/antioxidants as required
- perfume
- water as required up to 100

EXAMPLE 2

Formulation of a Cosmetic Composition According to the Invention Suitable as a Continuation Cosmetic Preparation:
- 0.5% by weight of pentapeptide of gly-pro-arg-pro-ala-$NH_2$ SEQ ID NO 1.
- 1% by weight of anise extract
- 0.5% of Magnesium gluconate
- 1% of acetyl tyrosyl-arginyl (Dipeptide)-1 cetyl Ester
- 5-7% of liquid paraffin
- 5-7% of polyisoprene
- 0.1-1% of stearylic alcohol 25-ethoxylate
- 1-2% of coccus-polypeptide of wheat
- 1-2% of wheat proteins esterified with palmitic acid
- 1-3% of glyceryl isostearate
- 1-3% of propylene glycol
- 2-3% of isostearylic alcohol
- 0-1% of lanolin oil
- 0-1% of panthenol
- preservatives/antioxidants as required
- perfume
- water as required up to 100

EXAMPLE 3

Formulation of a Cosmetic Composition According to the Invention Suitable as a Maintenance Cosmetic Preparation:
- 0.3% by weight of pentapeptide of gly-pro-arg-pro-ala-$NH_2$ SEQ ID NO 1.
- 0.5% by weight of anise extract
- 0.3% of Magnesium gluconate
- 0.5% of acetyl tyrosyl-arginyl (Dipeptide)-1 cetyl Ester
- 6% of liquid paraffin
- 5% of polyisoprene
- 0.5% of stearylic alcohol 25-ethoxylate
- 2% of coccus-polypeptide of wheat 2% of wheat proteins esterified with palmitic acid
2% of glyceryl isostearate
1% of propylene glycol
3% of isostearylic alcohol
0.5% of lanolin oil
0.5% of dimethicone
perfume
preservatives/antioxidants as required
water as required up to 100

EXAMPLE 4

In order to evaluate the efficacy of the preparation, object of Example 1, a self-evaluation test was effected on the part of a sample of 40 women aged between 35 and 65 years.

The volunteers applied the attack preparation to wrinkles for 20 days, using the syringe applier with a truncated end cannula.

The sample of women was made up as follows:
16 women aged between 35 and 45 years
12 women aged between 46 and 55 years
12 women aged between 56 and 65 years The preparation was applied at a dose of a milliliter specifically in the furrow of forehead wrinkles, glabellar wrinkles, eye contours, nose-labial wrinkles and lips contours. It was left to act for 10 minutes and was then massaged with the finger tips until its complete absorption.

The volunteers expressed a self-evaluation on the state of their expression and skin wrinkles in general at the end of the 20 days of treatment, by answering a questionnaire.

With the question: "Have you noticed a reduction in expression wrinkles?" the results were as follows:
  75% of the volunteers (30 out of 40 women) declared that they had noticed a reduction in expression wrinkles.
  In the sample consisting of 16 women aged between 35 and 45 years, 87.5% (14 women out of 16) declared they had noticed a reduction in expression wrinkles.
  In the sample consisting of 12 women aged between 46 and 55 years, 58.3% (7 women out of 12) declared they had noticed a reduction in expression wrinkles.
  In the sample consisting of 12 women aged between 56 and 65 years, 75% (9 women out of 12) declared they had noticed a reduction in expression wrinkles.

With the question: "After 20 days, did you notice an improvement in your skin with respect to smoothness and wrinkle relaxation?", the results were as follows:
  80% of the volunteers (32 women out of 40) declared they had noticed an improvement in their skin.
  In the sample consisting of 16 women aged between 35 and 45 years, 62.5% (10 women out of 16) declared they had noticed an improvement in their skin.
  In the sample consisting of 12 women aged between 46 and 55 years, 83.3% (10 women out of 12) declared they had noticed an improvement in their skin.
  In the sample consisting of 12 women aged between 56 and 65 years, 100% of the women declared they had noticed an improvement in their skin.

They were also asked to give an opinion on the use of the particular application method for the purpose of decreasing wrinkles. With the question "Do you find that the application method of the preparation on the furrow of the wrinkle with a syringe and cannula is useful for obtaining a decrease in wrinkles?", the results were as follows:
  92% of the volunteers (37 women out of 40) replied YES.
  In the sample consisting of 16 women aged between 35 and 45 years, 87.5% (14 women out of 16) replied YES.
  In the sample consisting of 12 women aged between 46 and 55 years, 100% replied YES.
  In the sample consisting of 12 women aged between 56 and 65 years, 91.7% (11 women out of 12) replied YES.

EXAMPLE 5

In vitro efficacy test on pentapeptide

The frequency of the contractions was determined in a nerve-muscle co-culture model to evaluate the decontracting capacity of pentapeptide gly-pro-arg-pro-ala-$NH_2$ SEQ ID NO 1, used at a concentration of 0.3% by weight.

After 1 minute and after 2 hours of incubation with the active principle being examined, the contractions verified over a period of 30 sec. were counted.

Figure 4:
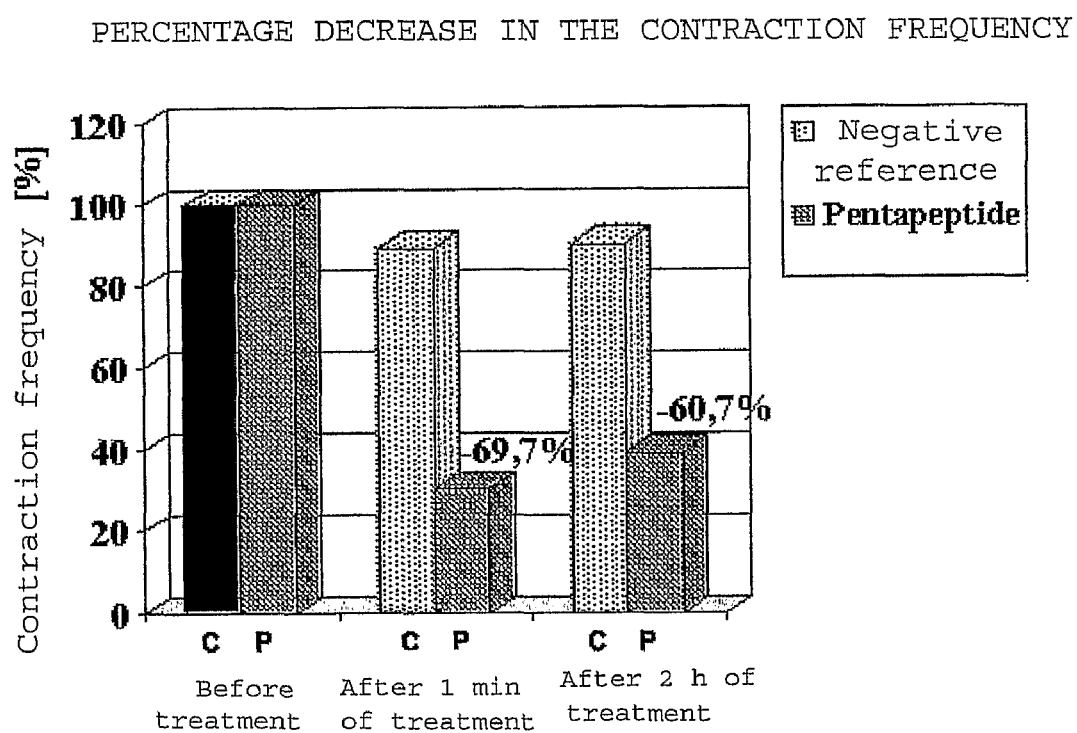
FIG. 4 is a graph which shows the percentage decrease in the contraction frequency before and after pentapeptide treatment.

With the use of 0.3% of said pentapeptide, the reductions in the frequency of the contractions were as follows:
  After 1 minute the average reduction in the contraction frequency was 69.75%
  After 2 hours the average reduction in the contraction frequency was 60.75% The data obtained are summarized in the graph illustrated in enclosed FIG. 4.

EXAMPLE 6

The activity was evaluated, of the two micro-elements Sodium and Potassium combined for the cosmetic application.

In Vitro Efficacy Test

The entity of the contraction was determined in a nerve-muscle model to evaluate the decontracting capacity of the Sodium-Potassium combination at 1, 2, 3%. The contractions verified over a period of 30 sec. were counted before the beginning of the treatment itself and after 20 minutes of contact of the co-culture with the active principle being tested.

The Sodium-Potassium combination shows a myorelaxing activity, reducing the muscular contractions to the following extent:
Sodium-Potassium 1%: −27%
Sodium-Potassium 2%: −86%
Sodium-Potassium 3%: −100%

These results are summarized in the graph illustrated in FIG. 1.

In Vitro Efficacy Test

The reduction in the surface, length and number of crow's feet wrinkles, glabellar and nose-labial wrinkles was evaluated in 20, 19, 20 volunteers respectively. These applied an emulsion containing Sodium-Potassium at 4% twice a day for 28 days. At the end of the 28 days, the following results were obtained:
Crow's Feet Wrinkles:
Total surface reduction: −40%
Total length reduction: −34%
Total number reduction: −13%

Improvements observed in 85% of the volunteers:
Glabellar Wrinkles
Total surface reduction: −20%
Total length reduction: −21%
Total number reduction: −18%

Improvements observed in 68% of the volunteers.
Nose-Labial Wrinkles
Total surface reduction: −22%
Total length reduction: −20%
Total number reduction: −17%

Improvements observed in 65% of the volunteers.

EXAMPLE 7

The decontracting efficacy was evaluated, of dipeptide N-acetyl tyrosyl-arginyl (Dipeptide) hexadecyl ester, dissolved in a hydro-glycol excipients.

The results obtained are summarized in the following Table.

| | DECREASE IN THE MUSCULAR FIBER CONTRACTION | | |
| --- | --- | --- | --- |
| | | Positive reference ($\alpha$- | Acetyl Dipeptide-1 Cetyl Ester (0.9%) |
| | Negative Reference | bungarotoxin) | After 5 min. After 2 hours |
| Fiber 1 | 0 | Blockage | >20% Blockage |
| Fiber 2 | 0 | Blockage | <20% Blockage |
| Fiber 3 | 0 | Blockage | <20% Blockage |

```
                        SEQUENCE LISTING

<160> NUMBER OF SEQ ID NOS: 1

<210> SEQ ID NO 1
<211> LENGTH: 5
<212> TYPE: PRT
<213> ORGANISM: Artificial
<220> FEATURE:
<223> OTHER INFORMATION: Active pentapeptide

<400> SEQUENCE: 1

Gly Pro Arg Pro Ala
1               5
```

In Vitro Efficacy Test
1. Evaluation of the gene expression of the POMC gene (relaxation neurohumor in a culture of human keratinocytes incubated for 24 h in the presence of acetyl dipeptide at 0.4%, 0.9% and 1.9%. With respect to the reference, the greatest over-expression of the gene being tested proved to be:
    acetyl Dipeptide-1 cetyl ester 0.9%>+29%
    acetyl Dipeptide-1 cetyl ester 1.9%>+63%
2. Evaluation of the CGRP synthesis (contraction neurohumor) in a culture of neurons incubated for 6 hours in the presence of acetyl dipeptide at 2.8% and 4.7%. With respect to the reference, the reduction in the CGRP synthesis is observed after incubation with dipeptide equal to:
    acetyl Dipeptide-1 cetyl ester 2.8%: −0%
    acetyl Dipeptide-1 cetyl ester 4.7%: −50%
3. Evaluation of the contraction frequency in a nerve-muscle co-culture model in incubation with acetyl Dipeptide-1 cetyl ester at 0.9% for 5 minutes and 2 h. The contraction of the 3 muscular fibers subjected to control decreases as follows:
    after 5 minutes of incubation with acetyl Dipeptide-1 cetyl ester 1 fiber out of 3 shows a contraction inhibition higher than 20%
    after 2 hours of incubation with acetyl Dipeptide-1 cetyl ester all 3 fibers show a contraction inhibition of 100%.

The invention claimed is:

1. A cosmetic composition suitable for relaxing expression wrinkles, said cosmetic composition comprising peptides with a decontracting action on muscular fiber wherein said peptides comprise a pentapeptide gly-pro-arg-pro-ala-NH$_2$ SEQ ID NO. 1 and a dipeptide tyrosine-arginine, at least one micro-element which reduces contraction of a muscular fiber and a cosmetically acceptable carrier.

2. The composition according to claim 1, wherein the at least one micro-element comprises sodium-potassium supplied in the form of an aqueous anise extract.

3. The composition according to claim 1, comprising a gly-pro-arg-pro-ala-NH$_2$ pentapeptide SEQ ID NO 1, an acetyl tyrosine-arginine-1 cetyl ester dipeptide, sodium, potassium, magnesium gluconate and a cosmetically acceptable carrier.

4. The composition according to claim 1, comprising from 0.001% to 5% weight of sodium and potassium, from 0.001% to 5% by weight of magnesium gluconate, from 0.001% to 5% by weight of acetyl tyrosylarginyl-1 cetyl ester and from 0.001% to 5% of gly-pro-arg-pro-ala-NH$_2$ pentapeptide SEQ ID NO. 1.

* * * * *